United States Patent
Kumar et al.

(10) Patent No.: US 7,678,070 B2
(45) Date of Patent: Mar. 16, 2010

(54) SYSTEM OF DAMPENING PRESSURE PULSATIONS CAUSED BY A POSITIVE DISPLACEMENT PUMP IN ENDOSCOPIC SURGERY

(76) Inventors: Atul Kumar, c/o Anil Hospital, C-13, Deepak Marg MD Road, Jaipur-302 004 (IN); Alka Kumar, c/o Anil Hospital, C-13, Deepak Marg MD Road, Jaipur-302 004 (IN)

( * ) Notice: Subject to any disclaimer, the term of this patent is extended or adjusted under 35 U.S.C. 154(b) by 1199 days.

(21) Appl. No.: 11/240,393

(22) Filed: Oct. 3, 2005

(65) Prior Publication Data
US 2006/0129099 A1    Jun. 15, 2006

(30) Foreign Application Priority Data
Nov. 30, 2004    (IN) .................... 2398/DEL/2004

(51) Int. Cl.
*A61M 1/00*    (2006.01)
(52) U.S. Cl. ...................... 604/31; 604/30; 604/151
(58) Field of Classification Search ............. 604/153, 604/30–35, 154; 417/471, 540, 477.1–477.14
See application file for complete search history.

(56) References Cited

U.S. PATENT DOCUMENTS

| | | | | |
|---|---|---|---|---|
| 2,811,931 A | * | 11/1957 | Everett ................. | 417/265 |
| 3,900,022 A | * | 8/1975 | Widran ................. | 600/105 |
| 4,650,462 A | * | 3/1987 | DeSatnick et al. ............ | 604/30 |
| 4,671,792 A | * | 6/1987 | Borsanyi ................... | 604/153 |
| 4,921,477 A | | 5/1990 | Davis | |
| 5,605,545 A | | 2/1997 | Nowosielski et al. | |
| 5,814,009 A | * | 9/1998 | Wheatman ................ | 604/21 |
| 6,396,583 B1 | * | 5/2002 | Clare ....................... | 356/436 |

FOREIGN PATENT DOCUMENTS

| | | |
|---|---|---|
| EP | 1 010 437 | 6/2000 |
| EP | 1 129 732 | 9/2001 |
| WO | WO 2006/024929 | 3/2006 |

OTHER PUBLICATIONS

F. Loffer, et al., "Hysteroscopic Fluid Monitoring Guidelines", *Journal of the American Assoc. of Gynecologic Laparoscopists*, Nov. 10, 1999.

* cited by examiner

*Primary Examiner*—Nicholas D Lucchesi
*Assistant Examiner*—Leah Stohr
(74) *Attorney, Agent, or Firm*—Dickstein Shapiro LLP

(57) ABSTRACT

A system for distending body tissue cavities of subjects by continuous flow irrigation during endoscopic procedures, the system including: a fluid source reservoir containing a non viscous physiologic fluid meant for cavity distension; a fluid supply conduit tube connecting the fluid source reservoir to an inlet port of a variable speed positive displacement inflow pump and an outlet port of the said inflow pump being connectable to an inflow port of an endoscope instrument through an inflow tube for pumping the fluid at a controlled flow rate into the cavity, the flow rate of the said inflow pump being termed as the inflow rate; an inflow pressure transducer being located anywhere in the inflow tube between the outlet port of the inflow pump and the inflow port of the endoscope; an outflow port of the endoscope being connectable to a waste fluid collecting container via a waste fluid carrying tube, and characterized in that an active inflow pressure pulsation dampening means is connected to the inflow tube for dampening the pressure pulsations inside the cavity created by the positive displacement inflow pump.

15 Claims, 3 Drawing Sheets

SYSTEM OF DAMPENING PRESSURE PULSATIONS CAUSED BY A POSITIVE DISPLACEMENT PUMP IN ENDOSCOPIC SURGERY

FIELD OF INVENTION

The present invention relates to a system for distending body tissue cavities of subjects utilizing continuous flow irrigation during endoscopic procedures. The system and the methods of the present invention described above can be used in any endoscopic procedure requiring continuous flow irrigation few examples of such endoscopic procedures being hysteroscopic surgery, arthroscopic surgery, trans uretheral surgery (TURP), endoscopic surgery of the brain and endoscopic surgery of the spine. The proposed invention can also have certain useful non medical applications.

BACKGROUND OF THE INVENTION

Endoscopic surgery is becoming increasingly popular because of the following reasons:
(a) it is a minimally invasive form of surgery,
(b) it avoids large incisions over the skin and muscle,
(c) it is associated with less pain,
(d) there is a relatively less requirement of blood transfusions and
(e) the patients can return back to normal work relatively early with minimal loss of working days.

While in the corresponding open conventional surgeries a relatively large body part consisting of skin and muscle needs to be cut in order to gain access to an underlying body tissue cavity, in endoscopic surgery instead of cutting body structures like skin and muscle an endoscope is introduced into the body cavity via the natural opening of a cavity, if such exists, or alternatively a minute hole is made in the wall of the cavity through which the endoscope is introduced to visualize the interior of the body tissue cavity and to perform major or minor endoscopic surgical procedures. For this reason endoscopic surgery is also sometimes called 'key hole' or 'minimal access surgery'. Besides reducing the pain associated with surgery, endoscopic surgery also helps in reducing the medical expenses.

Endoscopic Surgery is Primarily Related to a Tissue Cavity:

All endoscopic surgeries are carried out on a existing body cavity which is distended or 'ballooned up' by a suitable distending apparatus which permits the inner lining of the said tissue cavity to be visualized by the help of an endoscope. Though multiple endoscopic procedures have become established as the preferred surgical modality but still there is immense scope of increasing the safety and efficiency of the such existing endoscopic procedures by improving upon the existing techniques and apparatus used for distending body tissue cavities. Hysteroscopy, arthroscopy, TURP (transuretheral resection of the prostate), endoscopic surgery of the brain and endoscopic surgery of the spine are few of the routinely performed endoscopic procedures and the organs related to such surgeries being uterus, human joints, bladder, brain and the spine respectively. The list of endoscopic surgeries is long, ever increasing and there is hardly any body organ or organ system to which the benefits of endoscopy have not been extended.

Tissue Cavitiy is Initially Collapsed in its Natural State:

In the natural state tissue cavities are collapsed structures and the cavity walls are in apposition with each other as if kissing each other. Thus if an endoscope is introduced in such a collapsed cavity no endoscopic visualization is possible unless the cavity is ballooned up by filling it with a transparent fluid or a gas. Such ballooning of a tissue cavity is technically termed as 'cavity distension'. No endoscopic procedure can be performed without an efficient cavity distending system and no endoscopic procedure should be attempted without a safe distending system because unsafe tissue cavity distending means can lead to extreme human morbidity and even the death of a patient and such grim realities shall be discussed in the later sections of this manuscript. Cavity distension provides both endoscopic visualization and mechanical distension which is necessary for the movement of endoscopic instruments.

Continuous Flow Irrigation:

In the present invention, the Inventors are focused on a system for distending body tissue cavities for those endoscopic procedures in which the cavity needs to be distended by utilizing continuous flow irrigation only. Here, the term 'continuous flow irrigation' means that fluid simultaneously enters and escapes from a tissue cavity via separate entry and exit points, as a result of which a positive fluid pressure is created inside the tissue cavity which distends the cavity.

The Need for Continuous Flow Irrigation:

Any tissue cavity can be easily distended in a 'static manner' by simply pushing fluid via a single inflow tube inserted into the cavity and in this manner a desired cavity pressure can be developed and also maintained. For example, a cavity can be distended by pressing on the piston of a simple syringe filled with fluid with the outlet end of the syringe being connected to the cavity by a tube. Alternatively a fluid filled bottle may be elevated to a suitable height and under the influence of gravity fluid from such bottle may be allowed to enter the cavity via a tube connecting the said bottle to the cavity and in this manner a desired static pressure can be developed and also maintained. Though it is very easy to achieve distension by the said static manner, it is not a practical solution because blood and tissue debris which are invariably released from the fragile cavity inner lining mix with the distending fluid and endoscopic vision gets clouded within a few seconds or a few minutes. Thus continuous flow irrigation is needed to constantly wash away blood and tissue debris in order to maintain constant clear endoscopic vision.

Cavity Pressure and Cavity Flow Rate:

It is obvious that cavity fluid pressure and the flow rate through the cavity are the two basic parameters associated with all continuous flow irrigation systems.

An Efficient Distending System:

The Inventors believe that an efficient distending system is the one which provides a predictably continuous clear visualization and a predictably stable mechanical stabilization of the cavity walls. In order to achieve this the Inventors believe that a suitable stable constant precise cavity pressure and a suitable stable precise cavity flow rate have to be created and maintained in a predictable and controlled manner. The cavity pressure should be adequate so that vision is not clouded by oozing of blood and enough mechanical separation of the cavity walls occurs to allow the movement of the endoscope. Similarly, the cavity flow rate should be adequate enough to constantly wash away blood and tissue debris in order to allow clear vision. Many prior systems utilize a peristaltic pump over the inflow and or the outflow side and these peristaltic pumps create pressure pulsations which are then transmitted to the tissue cavity. Such pressure pulsations are undesirable and the main aim of the present invention is to dampen such pressure pulsations.

A Safe Distending System:

An efficient distending system as explained in the previous paragraph need not also be a safe distending system. In this regard, the Inventors would like to highlight that if the cavity pressure rises above the prescribed safe limits excessive fluid intravasation may occur or the cavity may even burst. Fluid intravasation is a process by which the irrigation fluid enters into the patient's body system through the cavity walls and may cause significant danger to the patient's life including death. Thus a safe distending system is one which prevents or minimizes fluid intravasation and allows the surgeon to accurately know the instantaneous real time rate of fluid intravasation into the patient's body system.

No Prior Art is Absolutely Safe:

Many different types of uterine distending systems are known and are being commercially marketed by many different companies but none of these systems can be considered to be absolutely safe for the patient. This fact has been clearly stated in the 'Hysteroscopic Fluid Monitoring Guidelines proposed by the Ad Hoc Committee on Hysteroscopic Fluid Guidelines of the American Association of Gynecologic Laproscopists February 2000 (Loffler F D, Bradley L D, Brill A I et al: Hysteroscopic fluid monitoring guidelines. The journal of the Americal Association of Gynecologic Laproscopists 7(1): 167-168, 1994) where the authors clearly and explicitly state "fluid pumps for low-viscosity media are a convenience and do not guarantee safety". The present invention aims at providing a distending system which is both safer and more efficient in comparison to all the prior art systems.

Basic Physics of Cavity Distension:

Although, a person skilled in the art may know it, the Inventors would like to provide a brief description of the basic physics of cavity distension. Filling the tissue cavity with fluid enables distension of the same. Initially more fluid is pumped in than the amount which is extracted from the cavity and ultimately the inflow rate is fixed at a level where a somewhat desired cavity pressure and distension is achieved.

Brief Description of an Endoscope:

Prior to describing the basic layout of a continuous flow irrigation system the basic structure of an 'endoscope' needs to be described. Endoscope is a cylindrical tube having an outer diameter ranging between 3 to 9 mm approximately. A typical endoscope has four channels. One channel is meant to pass a fibereoptic telescope while endoscopic instruments are negotiated through a second instrument channel. A third channel also known as the inflow channel is used for pushing irrigation fluid into a tissue cavity, the proximal end of this channel ending in a metal adaptor known as the inflow port while the distal end of this inflow channel opens near the tip of the endoscope. The inflow port is connectable to an inflow tube which carries sterile irrigation fluid from a fluid source reservoir. A fourth channel also known as the out flow channel is meant for extracting waste fluid out of the cavity, the proximal end of this channel ending in a metal adaptor known as the outflow port while the distal end of this outflow channel opens near the tip of the endoscope. The outflow port is connectable with an outflow tube which transports the waste fluid from the cavity to a suitable waste fluid collecting reservoir. A set of fiber optic bundles contained inside the telescope transmit light energy produced by an external light source. This light energy illuminates the walls of the tissue cavity. The image thus formed is carried via a separate set of optical pathways again situated inside the telescope. A video camera attached to the eye piece of the telescope forms a clear endoscopic image of the cavity on a TV monitor. The endoscopic surgeon has to continuously look at the TV monitor all through the endoscopic procedure.

Basic Layout of a 'Continuous Flow Irrigation System:

Henceforth in this manuscript unless otherwise specified the term 'distension' shall be deemed to imply tissue cavity distension by 'continuous flow irrigation' only and the term 'cavity' unless specifically stated shall be deemed to refer to a 'body tissue cavity'. In a typical distension system a physiological non viscous liquid like 0.9% normal saline, 1.5% glycine, mannitol, ringer's lactate and 5% dextrose is stored in a sterile fluid source reservoir. A fluid supply tube connects the said fluid reservoir with the inlet end of a pump. The outlet end of the inflow pump is connected to the inflow port of an endoscope. When the inflow pump operates the fluid from the fluid source reservoir is sucked via the fluid supply tube and the inflow pump pushes this fluid into the tissue cavity via the said inflow tube. The pump operates by consuming certain amount of energy and as a result of this a positive fluid pressure is created inside the tissue cavity. An outflow tube extends between the outflow port and the inlet end of an outflow pump. When the outflow pump operates it actively extracts waste fluid from the cavity again at the expense of energy and this waste fluid is ultimately sent to a waste fluid reservoir via a tube which connects the outlet end of the outflow pump with the waste fluid reservoir. Alternatively the outflow pump may be missing and in such case the outflow tube directly carries the waste fluid from the cavity to the waste fluid reservoir and the energy for such act is supplied by gravity instead of the outflow pump. Also, the inflow pump may be missing and in such case the inflow tube directly supplies the irrigation fluid from a fluid source reservoir to the cavity. In such case the fluid source reservoir is hung at a suitable height above the patient and the said energy for cavity distension is derived from gravity instead of the inflow pump. A suitable pressure transducer is attached to the inflow tube, the outflow tube or directly to the cavity to measure the fluid pressure. A controller may be incorporated to regulate the system.

The Simplest Continuous Flow Irrigation System:

In its simplest form, a continuous flow irrigation system comprises a fluid reservoir bottle hung at a suitable height above the patient and an inflow tube connecting this fluid reservoir to a tissue cavity. An out flow tube is incorporated to remove fluid from the tissue cavity. In this system there is no pump and no transducer. In such a system fluid flows from the fluid source reservoir into the cavity and the required energy is supplied by gravity. The pressure developed inside the cavity can be increased or decreased by elevating or lowering the height of the fluid source reservoir. In such system the main limiting factor is the height of the room ceiling beyond which the fluid reservoir cannot be raised. This is a crude system having negligible practical importance and has been included only from the academic point of view. Also in such a system unlimited volume of irrigation fluid may enter into the patient's blood circulation. Thus such system is not suitable even from the patient safety point of view.

Basic Components of a Continuous Flow Irrigation System:

Like a motor car is made up of certain obvious components like engine, tyres and a steering wheel, a continuous flow distending system is made of components like pump, pressure transducer, flow regulating valve, rubber tubes and a controller. The pump may be a positive displacement pump like a peristaltic pump, piston pump or a gear pump or alternatively it may be a dynamic pump like a centrifugal pump. The said pump may be attached on the inflow side only, on the outflow side only or both on the inflow and outflow side. Further if a pump is attached only on the inflow side the outflow tube may directly empty in a waste fluid reservoir at atmospheric pressure or a vacuum source may also be additionally attached. In some distending systems a flow controlling valve is attached on the outflow tube in order to regulate the cavity pressure. There may be a single pressure transducer attached to the inflow tube, the outflow tube or directly to the cavity. In some systems instead of one pressure transducer two pressure transducers may be used, one on the inflow tube and the other on the outflow tube.

Pressure Pulsations Caused by Positive Displacement Pumps

In certain prior art systems a positive displacements have been used on the inflow side, the outflow side or on both inflow as well as outflow side of the irrigation circuit. Such positive displacements, like peristaltic pumps, create pressure pulsations which are transmitted to the tissue cavity. Such pressure pulsations are undesirable as they lead to turbulence inside the tissue cavity. In the U.S. Pat. No. 5,520,638 a variable speed peristaltic pump is used to push irrigation fluid into a tissue cavity. This patent is related to the 'Continuous Wave II Arthroscopy Pump' marketed by Arthrex. A chamber with volume is connected to the inflow tube and a collapsible bladder is contained within the bladder. The collapsible bladder has an open end connected with tubing to a pressure transducer. Once activated the pump begins to introduce fluid into the tissue cavity via the inflow tube and as pressure builds within the tissue cavity, fluid enters the chamber, and air in the chamber is compressed. The compressed air in the chamber compresses the bladder. Air pressure in the bladder is experienced by the pressure transducer. The pressure transducer feeds pressure information to a controller which regulates the RPM of the pump on the basis of a pressure feedback mechanism. Thus by the help of a pressure feedback mechanism the pressure inside a tissue cavity is maintained by fluctuating around a desired value. In this invention an important purpose of the said chamber is to dampen the pressure pulsations created by the peristaltic pump. Such pressure pulsations create turbulence inside the tissues cavity and are hence undesirable. The method of dampening the pressure pulsations as described in this U.S. Pat. No. 5,520,638 is not adequately efficient, especially at high pump RPM's. In the present invention a method shall be described by which the amplitude of the said pressure pulsations would be reduced to negligible magnitude even at a high pump RPM.

Some other prior art systems use a peristaltic pump on the inflow side while the outflow tube directly drains into a waste collecting reservoir at atmospheric pressure or a vacuum source is attached to it and examples of such systems are seen in U.S. Pat. No. 4,650,462 (DeSatanick et al), U.S. Pat. No. 4,998,914 (Weist et al), U.S. Pat. No. 5,460,490 (Carr et al) and U.S. Pat. No. 6,159,160 (Hsei et al). Some examples of such commercial products are Hamou Endomat (Karl Storz, Tuttinglheim, Germany), Hamou Hysteromat (Karl Storz, Tuttinglheim, Germany), Uteromat Fluid Control of Olympus company, Hystero Pump II 222 of Richard Wolf company, Arthropump (Karl Storz, Tuttinglheim, Germany) and Apex Universal Irrigation System of Linvatec Corporation.

In one of the prior art documents, U.S. Pat. No. 5,152,746 (Atkinson et al) a piston pump has been incorporated on the inflow side while the outflow tube simply drains into a waste collecting reservoir at atmospheric pressure.

In U.S. Pat. No. 5,814,009 (Wheatman) a pneumatic pump situated on inflow side inflates a bladder with air, wherein inflation of said bladder exerts a force against the supply of fluid to deliver fluid there from and the product is commercially marketed as Dolphin II Fluid Management System by ACMI CIRCON. In this system the outflow tube directly empties into a waste collecting reservoir at atmospheric pressure or with a vacuum source attached to it.

OBJECTS OF THE INVENTION

The overall objective of the invention is to provide a turbulence free system for distending body tissue cavities for those endoscopic procedures which utilize continuous flow irrigation.

The main object of the invention is to minimize the amplitude of pressure pulsations, inside the tissue cavity, created by an inflow positive displacement pump to almost negligible levels even at relatively high pump RPM.

Another object of the invention is to minimize the frequency of pressure pulsations, inside the tissue cavity, created by an inflow positive displacement pump, without reducing the inflow pump RPM.

Another objective of the invention is to provide a method of determining the real time rate of fluid intravasation by utilizing two fluid flow rate sensors, one on the inflow tube and another on the outflow tube.

SUMMARY OF THE INVENTION

The present invention provides a system for distending body tissue cavities for those endoscopic procedures which utilize continuous flow irrigation. The main aim of the invention is to minimize tissue cavity turbulence by minimizing the amplitude as well as the frequency of the pressure pulsations created by an inflow positive displacement pump. A peristaltic pump situated on the inflow side pushes fluid into a body tissue cavity via an inflow tube while an outflow tube drains directly into a waste fluid collecting container at atmospheric pressure or having a vacuum source attached to it. A 'pressure pulse dampening system' is used to reduce the amplitude of pressure pulsations created by the inflow peristaltic pump.

DETAILED DESCRIPTION OF INVENTION

Figure 1:
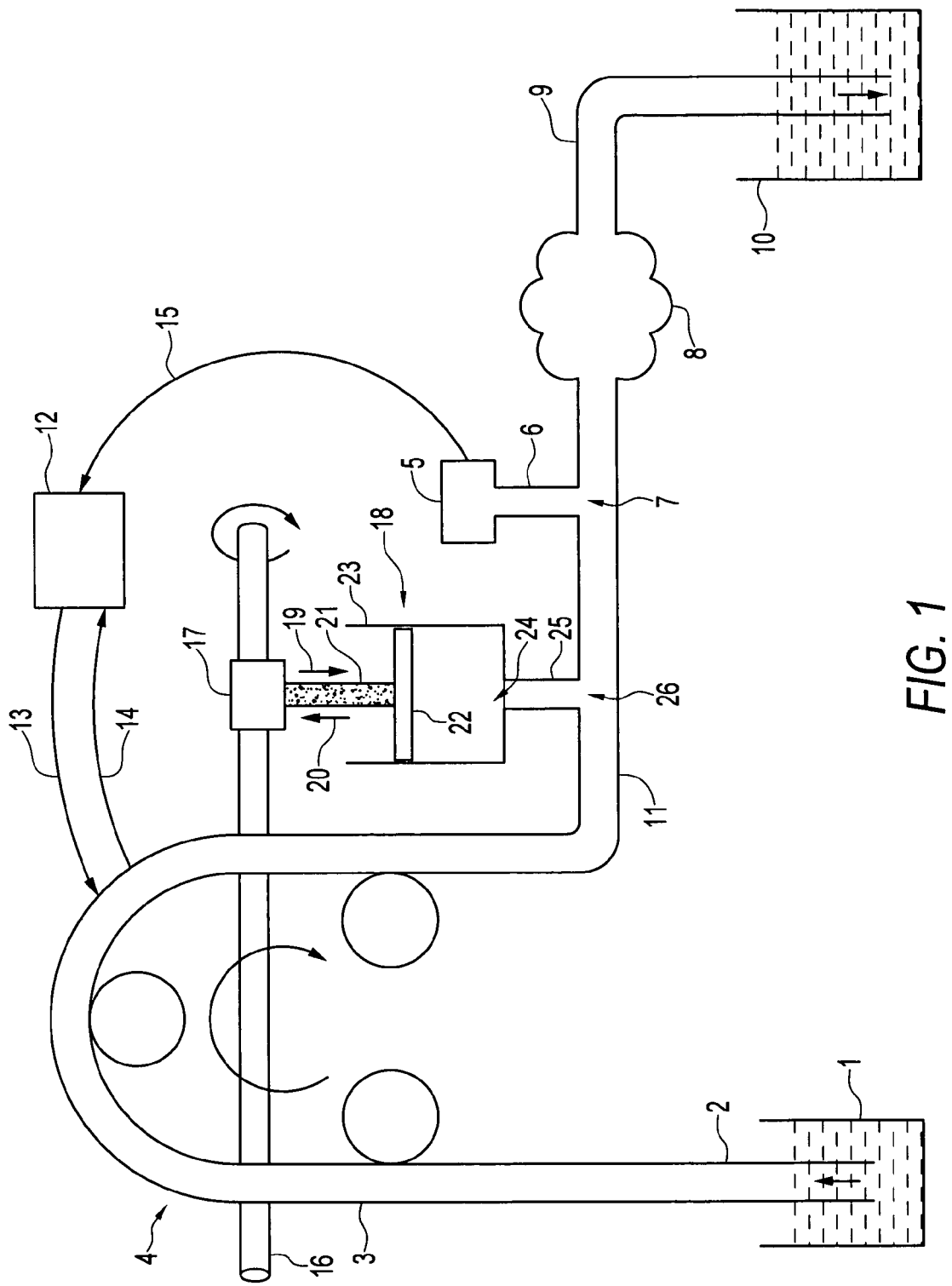
FIG. 1 shows the main invention.

Accordingly, the present invention provides a system for distending body tissue cavities of subjects by continuous flow irrigation during endoscopic procedures the said system comprising:

a fluid source reservoir containing a non viscous physiologic fluid meant for cavity distension;

a fluid supply conduit tube connecting the fluid source reservoir to an inlet port of a variable speed positive displacement inflow pump and an outlet port of the said inflow pump being connectable to an inflow port of an endoscope instrument through an inflow tube for pumping the fluid at a controlled flow rate into the cavity, the flow rate of the said inflow pump being termed as the inflow rate;

an inflow pressure transducer being located anywhere in the inflow tube between the outlet port of the inflow pump and the inflow port of the endoscope;

an outflow port of the endoscope being connectable to a waste fluid collecting container via a waste fluid carrying tube, and characterized in that an active inflow pressure pulsation dampening means is connected to the inflow tube for dampening the pressure pulsations inside the cavity created by the positive displacement inflow pump.

In an embodiment of the present invention, the fluid source reservoir containing the non-viscous physiologic fluid is maintained at atmospheric pressure or at a pressure greater than the atmospheric pressure.

In another embodiment of the present invention, a proximal open end of the fluid supply tube is connected to the fluid source reservoir and a distal end of the tube is connected to the inlet end of the variable speed positive displacement inflow pump.

In yet another embodiment of the present invention, the proximal open end of the fluid supply tube is constantly and completely immersed in the fluid source reservoir.

In still another embodiment of the present invention, a proximal end of the inflow tube is connected to the outlet end of the variable speed positive displacement inflow pump and a distal end of the inflow tube being connectable to the inflow port of the endoscope instrument.

In one more embodiment of the present invention, the variable speed positive displacement inflow pump is selected from the group comprising peristaltic pump, piston pump, gear pump and diaphragm pump.

In one another embodiment of the present invention, the variable speed positive displacement inflow pump is a peristaltic pump.

In a further embodiment of the present invention, the inflow pressure transducer is located sufficiently away from the cavity site, preferably near the outlet end of the inflow pump from the practical point of view, such that an almost actual pressure inside the cavity is measured.

In a further more embodiment of the present invention, a proximal end of the waste fluid carrying tube being connectable to the outlet port of the endoscope instrument and a distal end of the waste fluid carrying tube is connected to the waste fluid collecting container.

In another embodiment, the system of the present invention further comprises a micro-controller means electrically coupled to the inflow pressure transducer and the inflow pump for regulating the operation of the inflow pump.

In yet another embodiment of the present invention, the fluid supply tube, the inflow tube and the waste fluid carrying tube are flexible, disposable and are made of polymeric material.

In still another embodiment of the present invention, the active inflow pressure pulsation dampening means comprises a single outlet syringe mechanism, the piston of the same being coupled synchronously to the positive displacement inflow pump through a coupling means and a single outlet end of the said syringe mechanism being connected to the inflow tube.

In one more embodiment of the present invention, the active inflow pressure pulsation dampening means is connected to the inflow tube between the outflow end of the peristaltic pump and the point where the inflow pressure transducer is located.

In one another embodiment of the present invention, the fluid source reservoir, the inflow pump, the tubes and the tissue cavity are placed approximately at the same height with respect to a horizontal ground.

In a further embodiment of the present invention, the variable speed inflow peristaltic pumps is provided with one to five peristaltic pump tubes connected in parallel between the inflow and outflow ends of the peristaltic pump for reducing the frequency of pulsations in the pressure, the said tubes being connected to each other at the inflow and outflow ends of the peristaltic pumps, and the said peristaltic pump tubes being the ones which come in contact with the rollers of the peristaltic pumps.

Figure 2:
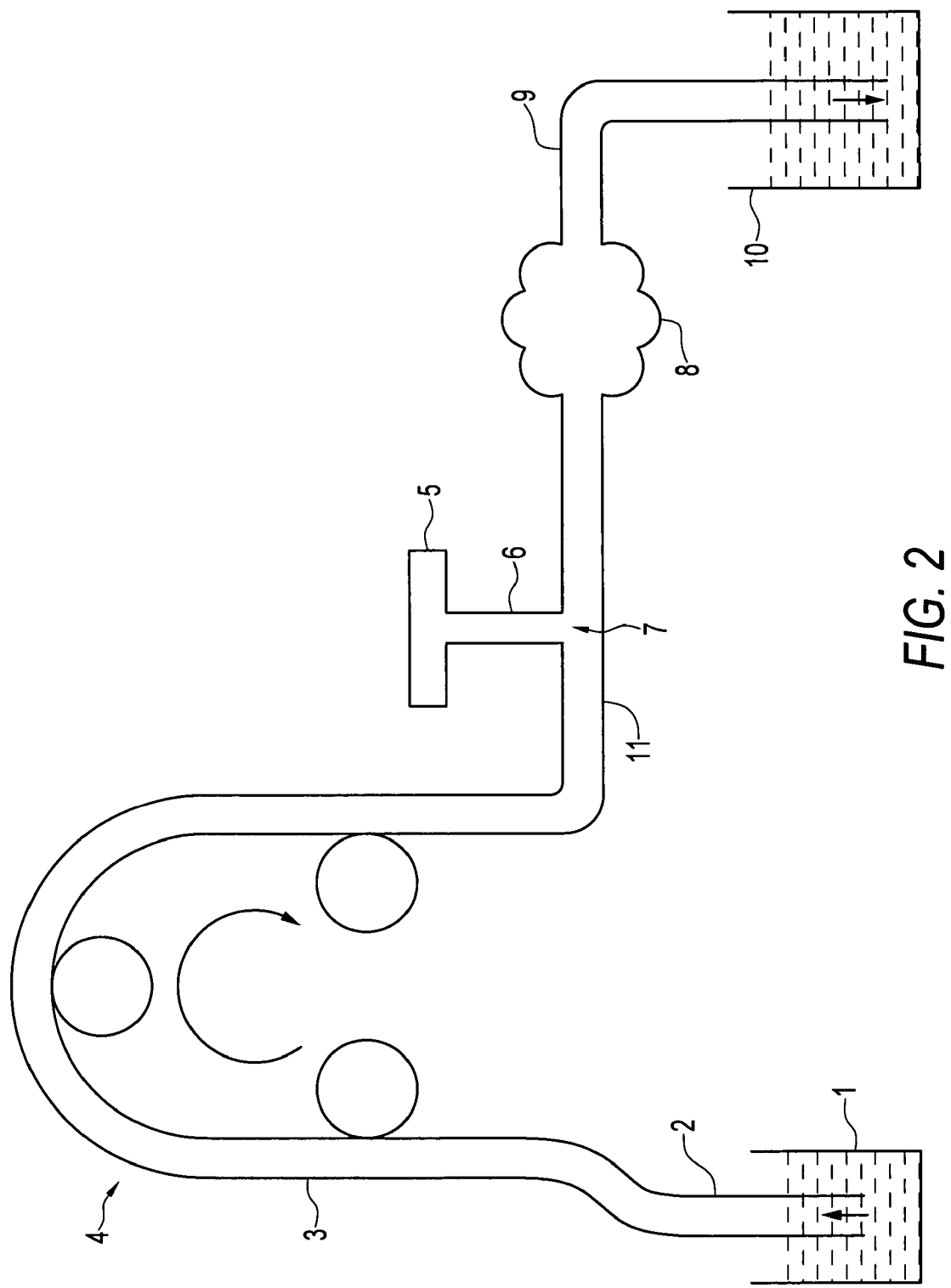
FIG. 2 is the same as FIG. 1 except that the 'pressure pulse dampening system' and the controller have not been included.

FIG. 1 shows the main invention, which is similar to FIG. 2, which represents the prior art system except that a 'pressure pulse dampening system' 18 and a controller 12 have been included. Although, the controller 12 is included in FIG. 1, it is an optional feature, without which the device of the present invention can work.

Referring to FIG. 2, a peristaltic pump 4 situated on the inflow side pulls sterile irrigation fluid from a fluid source reservoir 1 via a fluid delivery tube 2. One end of the fluid delivery tube is constantly immersed in the fluid source reservoir 1 while the other end of tube 2 is connected to an inlet end of the peristaltic pump 4. A proximal end of an inflow tube 11 is connected to the outlet end of the pump 4 while the distal end of tube 11 is connected to the inflow port of an endoscope. A suitable pressure transducer 5 is fluidly connected to the inflow tube 11. The pressure transducer measures the fluid pressure inside the inflow tube such as at a point 7. When the pump 4 rotates in the direction of the curved arrow the irrigation fluid is pushed into the tissue cavity 8 via the inflow tube 11 as a result of which the cavity 8 distends. Waste fluid from the cavity is transported to a waste fluid collecting container 10 via an outflow tube 9. The container 10 can be at atmospheric pressure a vacuum source may be attached to it.

The flow rate of the inflow pump, that is the inflow rate, is being termed as R1 and the pressure measured by the pressure transducer 5 is being termed as P. The rate at which the waste fluid from the cavity 8 escapes via the outflow tube 9, that is the outflow rate, being termed as R2. The pressure measured by the pressure transducer 5 is being termed as P. P is supposed to represent the actual pressure inside the cavity 8, however in practical situation the value P is always found to be slightly more than the actual pressure inside the cavity 8 due to resistance imposed by the inflow tube to the flow of fluid.

A Method to Dampen the Pressure Pulsations of the Inflow Peristaltic Pump

Referring to FIG. 1 the fluid pressure, such as at a point 26, is pulsatile in nature because the peristaltic pump 4 pushes fluid via its outlet end in the form of pulses and not in a continuous manner. Hypothetically assuming that the pump 4 rotates at fixed RPM then in that case the frequency of such pulsations would remain uniformly the same all through the operation of the pump. If a graph is plotted for the said pulsations, by relating the fluid pressure to the 'Y' axis and the time to the 'X' axis, then such graph would have a uniform shape having positive and negative pressure swings of a predictably fixed amplitude and fixed frequency. It is to be noted that as the pump RPM is increased the frequency as well as the amplitude of the said pressure swings also increase. The said pulsations are produced because each time any one roller of the peristaltic pump comes in apposition with a fixed point, for example the outlet end of the peristaltic pump, some fluid is pushed out from the outlet end of the pump in the form of a bolus. The wave form of such pulsations need not be sinusoidal, but for the sake of an easier understanding let the said waveform be hypothetically assumed to be sinusoidal in nature. As already stated, if the pump RPM increase then along with the frequency the amplitude of the said waveform also increases. When the pump 4 rotates in the direction of the curved arrow fluid tends to accumulate in the inflow tube 11, the cavity 8 and the outflow tube 9 and let this region into which the fluid tends to accumulate, be termed as 'fluid accumulation region'. In physical terms the said pressure pulsations are produced because the fluid tends to accumulate in the 'fluid accumulation region' in the form of regular pulses wherein each pulse corresponds to a fixed volume of fluid pushed by a roller into the 'fluid accumulation region' in the form of a bolus of fluid. Thus the motion of each roller would correspond to one complete sinusoidal pressure wave. The movement of a single roller in relation to a fixed point such as the outlet end of the pump can be hypothetically divided into three parts, that is, part one when the roller approaches the said point, part 2 when the roller is in apposition with the said point and part 3 when the roller moves away from the said point. Let the parts 1, 2 and 3 be collectively termed as 'single roller movement' and the time taken to accomplish the said 'single roller movement' be termed as 'single roller time'. Assuming the pressure waveform to be a sinusoidal curve, each 'single roller movement' corresponds to one complete sinusoidal pressure waveform consisting of a positive pressure surge followed by a negative pressure surge or vice versa. Also the time period of the assumed sinusoidal wave form would be equal to 'single roller time'. If during the positive pressure surge an adequate volume of fluid is removed from the 'fluid accumulation region' and during the negative pressure surge the same adequate volume of fluid is again added back into the 'fluid accumulation region' the sinusoidal nature of the pressure waveform could get dampened and the resultant waveform would get transformed into an almost straight line curve. The resultant waveform could theoretically be an absolute straight line if the wave form associated with the said process of adding and removing adequate volumes of fluid from the 'fluid accumulation region' absolutely resembled with the wave produced as a result of the pulsatile flow of the peristaltic pump and the phase difference between the two waves was exactly 180 degrees however this may not be achieved in practical situations. However a substantial dampening of the resultant waveform could be practically achieved if a syringe system was synchronously coupled with the inflow peristaltic pump 4 and the single outlet end of the said syringe system was connected with the 'fluid accumulation region'. Referring to FIG. 1, this figure is the same as FIG. 2 except that a said syringe system 18 has been included. The syringe system 18 consists of a piston 22 denoted by a shaded area. The piston 22 moves up and down inside a cylinder 23 while making a watertight contact with the inner walls of this cylinder 23. One end of a straight rod 21 is connected to the piston while the other end of this rod 21 is connected to a coupling mechanism 17 housed on a common shaft 16. The coupling mechanism 17 and the peristaltic pump 4, both are attached on to a common shaft 16. The coupling mechanism 17 is so designed that it converts the rotary motion of the shaft 16 into a linear up down motion of rod 21 which is ultimately manifested as an up down movement of piston 22 inside the cylinder 22. The up down motion of the rod 21 is denoted by arrows 19 and 20. Thus the shaft 16 is a common shaft which mechanically operates both, pump 4 as well as the syringe system 18. The direction of rotation of the shaft 16 is denoted by a curved arrow located at the right end of the shaft 16. The syringe system 18, as the name suggests, resembles a hypodermic syringe used for giving injections to patients. Obviously, the syringe system 18 has only one single opening 24. A tube 25 extending between the opening 24 and the inflow tube 11 connects the syringe system to the inflow tube 11. Tube 11 is a part of the said 'fluid accumulation region' described in this paragraph. Thus the syringe system can be considered to be connected with the said 'fluid accumulation region'. The opening 24 can be referred to as an 'outlet end' or an 'inlet end' because the syringe system can push as well as pull fluid from the 'fluid accumulation region'. However for the sake of convenience henceforth the opening 24 shall be termed as the outlet end of the syringe system 18. The coupling mechanism 17 is so designed that the vertical movements of the syringe system can be accurately synchronized with the rotary motion of the peristaltic pump 4. The piston 22 can move up>down>up or down>up>down, depending upon the initial position of the piston at the start of the motion and let each such movement of the piston be termed as a 'complete piston movement'. The coupling mechanism 17 is so designed that while the peristaltic pump 4 rotates by 360 degrees the syringe system correspondingly exhibits 'complete piston movements' which are equal to the number of the rollers of the peristaltic pump. Thus for a peristaltic pump which has three rollers then for each 360 degrees rotation of the peristaltic pump the syringe system exhibits three 'complete piston movements' while for a peristaltic pump with four rollers four 'complete piston movements' would occur for each 360 degree rotation of the peristaltic pump. The syringe system is synchronized with the peristaltic pump via the coupling mechanism 17 in such manner that while a roller of the peristaltic pump produces a positive pressure pulse the syringe system extracts fluid out from the 'fluid accumulation region' and while the same roller produces a negative pressure pulse the syringe system pushes an equivalent volume of fluid back into the 'fluid accumulation region'. In order to dampen the pulsations of the peristaltic pump, besides mechanically synchronizing the syringe system with the peristaltic pump the volume of fluid pulled in or pushed out of the syringe system corresponding to each upward or downward movement of the piston also has to be adjusted accurately, and the same may be done manually by a 'hit and try method'. The volume of fluid pulled in or pushed out by the syringe system depends upon the linear movement excursion of the piston 22. Also the magnitude of the downward piston excursion is equal to the magnitude of the upward piston excursion, thus the volume of fluid pushed out is always equal to the volume of fluid pulled in during each downward or upward movement. Thus the coupling mechanism 17 has two functions, synchronization of the syringe system with the peristaltic pump and adjusting the volume of fluid pulled in or pushed out by the syringe system for each upward or downward movement of the piston. The synchronization and the determination of the said volume to be pushed out or pulled into the syringe system are done manually such that a substantial dampening of the pressure pulsations is achieved and once this is achieved the synchronization at the level of the coupling 17 is never again disturbed and the volume of fluid pulled in or pushed out of the syringe system for each movement excursion is also not changed thereafter. After the coupling 17 is adjusted with respect to synchronization and the volume of fluid to be pulled in and pushed out, the peristaltic pump pulsations shall continue to remain dampened independent of the peristaltic pump RPM and the nature of rotation, that is fixed or variable RPM. In simpler terms the peristaltic pump pulsations would continue to remain dampened even at a high pump RPM. Also the point at which the syringe system 18 is connected to the said 'fluid accumulation region', for example the inflow tube 11, then the position of such a point should also not be changed thereafter because this may bring about a phase difference between the waveform related to the peristaltic pump pulsations and the waveform related to the syringe system pulsations, thus the resultant dampening could no longer be satisfactory. Also preferably the outlet tube 25 of the syringe system should be connected as close to the outlet end of the inflow peristaltic pump as possible.

Figure 3:
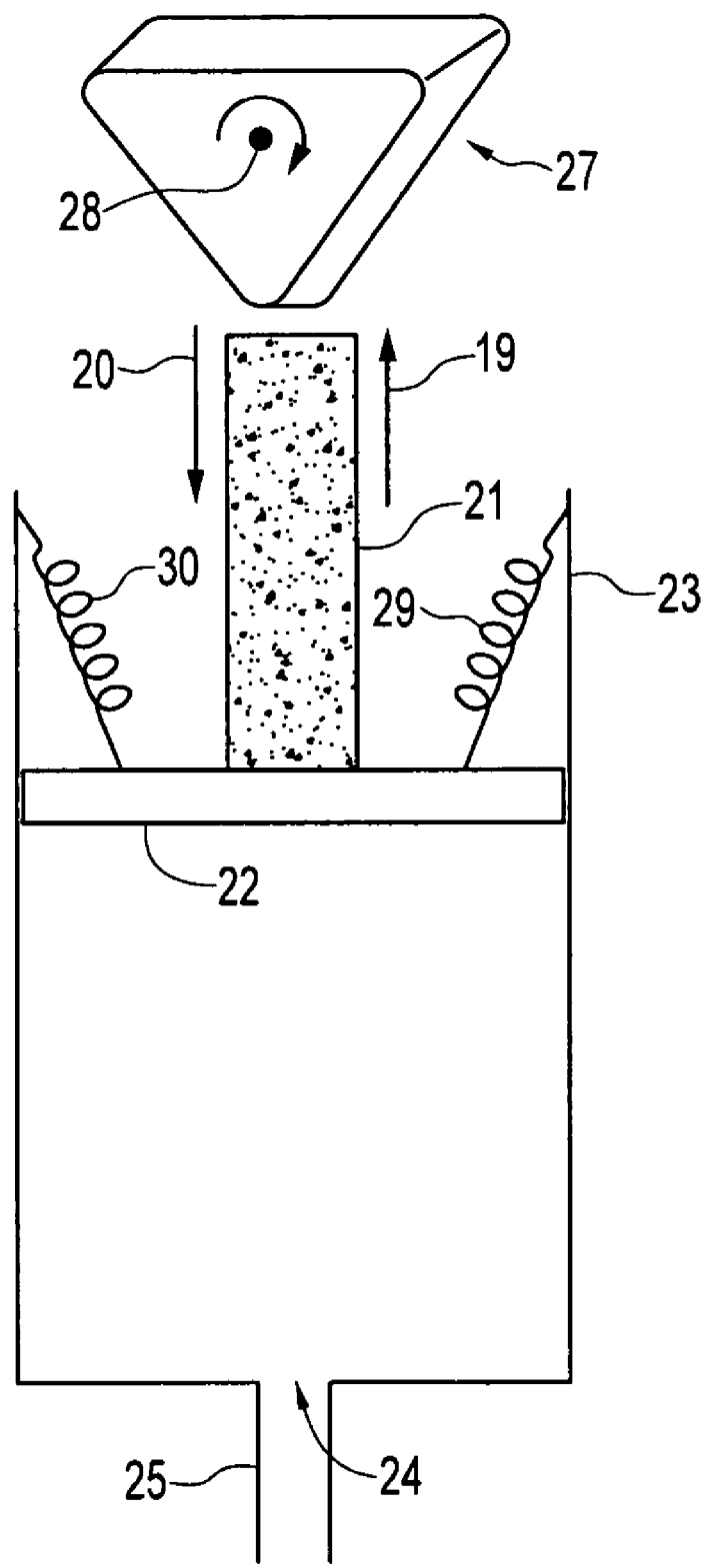
FIG. 3 describes the 'pressure pulse dampening system' in detail.

The coupling 27 can be compared to some extent with the conventional CAM system present in automobile engines. Any specific mechanical design for the coupling 17 is not important, it is the resultant function of the coupling 17 with respect to the piston movement, as already described, which is important. The coupling 17 can have many mechanical designs. FIG. 3 shows one such possible mechanical design for the coupling 17. In FIG. 3 a small length of the common shaft 16, which is related to the coupling 17, has been made of triangular shape as seen in its cross sectional view and the same is labeled as 27. Let this triangular part 27 be termed as the 'piston coupler'. The edges of the piston coupler are shown sharp however they could preferably be rounded to suit various operational needs. Similarly the size of the 'piston coupler' could also be increased or decreased in order to decrease or increase the volume of fluid displaced by the cylinder during a downward or upward movement of the piston. The central axis point of the 'piston coupler' is denoted by point 28. In case the dimensions of the 'piston coupler' are chosen to be relatively larger than the dimension of the common shaft 16, the point 28 could also represent the point at which the common shaft 16 passes through the 'piston coupler' and in such a situation the 'piston coupler' 27 could be manually rotated on the common shaft 16 in a clockwise or anti clockwise direction and then locked mechanically at a position which provides the most accurate synchronization. The springs 29 and 30 extending between the inner walls of the cylinder and the piston exert a constant and substantially large upward pull on the piston 22 which causes the rod 21 to constantly be in apposition with the 'piston coupler' 27. The springs can be one or more than one in number and the springs can also be substituted by any other mechanical means also which provide an active upward movement of the piston. The 'piston coupler' 27 is assumed to be able to apply a substantially large downward force on the piston 22 via rod 21 such that a corresponding transient negative fluid pressure pulse inside the cylinder can be totally neglected in the face of the said large substantial downward force. Similarly the springs 29 and 30 are capable of pulling up the piston with a substantially large force such that a corresponding transient positive fluid pressure pulse inside the cylinder could be totally neglected. The idea is that the downward movement of the piston should not be aided by the transient negative pressure pulse inside the cylinder, this downward movement should be an active movement for which energy is to be derived from the springs from the shaft 16. Similarly the upward movement of the piston should not be aided by the transient positive pressure pulse inside the cylinder, this upward movement should be an active movement for which energy is to be derived from the springs 29 and 30. The energy for the said upward movement of the piston could also be derived from the shaft 16 if suitable mechanical provision facilitating an active upward movement of the piston could be provided at the level of the coupling 17.

It is important to note that it is not mandatory to use the said 'pressure pulse dampening system' with a peristaltic pump only as, with suitable mechanical modifications, the 'pressure pulse dampening system' could be used beneficially with any type of a positive displacement pump.

The 'pressure pulse dampening system' could also be a mechanism like the 'piston coupler' 27 shown in FIG. 3 whose rounded edges could directly impinge on a suitable area situated on the outer surface of the 'fluid accumulation region' in a uniform synchronized manner, as described, such that this results in continuous uniform synchronized variations in the total volume capacity of 'fluid accumulation region'. The said suitable area on the outer surface of the 'fluid accumulation region' could be a membrane made consisting of a strong resilient polymeric material having an adequate elasticity. The said membrane should also be sufficiently thick and should have an adequate elasticity such that an outward movement of such membrane, a movement related to the upward pull by the said springs, applied a substantially larger force in comparison to force related with the transient corresponding pressure pulse.

Referring again to FIG. 1 the pressure transducer 5 sends an electrical signal to the controller 12 via wires 15 and on the basic of this signal the controller 12 regulates the RPM of the inflow pump 4 corresponding to a preset desired pressure value. At the start of the surgery the surgeon feeds a desired cavity pressure value P. Next the inflow pump 4 is operated and upon a pressure feedback mechanism the controller makes the pump 4 to operate at some RPM at which the desired cavity pressure is maintained. Thus the cavity pressure is maintained by fluctuating around a desired preset value.

The pressure dampening mechanism used in the present invention is an active pressure dampening system and not a passive dampening system. The Applicants have realized that only active pressure dampening systems as discussed above provide substantial dampening to the pressure pulsation caused by the peristaltic pumps and relying on passive factors such as the inherent resistance to the flow of the liquid etc do not provide any effective pressure dampening. Further, the pressure dampening system may not provide any substantial dampening to the pressure pulsation caused by the physiological contractions of the cavity walls.

A System of Incorporating Multiple Peristaltic Pump Tubes

In the preceding parts of the manuscript the peristaltic pumps 4 is shown to have only a single tube, 3, which come in contact with the rollers of the peristaltic pump 4. Arbitrarily referring to the inflow pump 4, $$R1 = \frac{\pi \times B^2 \times L}{4} \times RPM$$

where R1=Flow rate of pump 3, B=inner diameter of the peristaltic pump tube 3, L=length of tube 3 and RPM=revolution per minute of pump 4. If the value B is doubled then for the same RPM the flow rate R1 doubles. Similarly if L doubles then also for the same RPM the flow rate R1 doubles. However keeping in mind the mechanical constraints the values B and L cannot exceed a certain practical value. However if two tubes like tube 3 are used in parallel in the pump 4 then mathematical expression for the flow rate could be written as follows:

$$R1 = \frac{\pi \times B^2 \times L}{4} \times RPM \times 2$$

This implies that if two peristaltic pump tubes are used instead of one single tube then the flow rate becomes double for the same RPM and if three tubes are used then the flow rate becomes three times and so on. The frequency of the 'pressure pulsations' created by a peristaltic pump is directly proportional to the pump RPM. The said 'pressure pulsations' are undesirable thus it is helpful to keep their frequency as minimal as possible if the flow rate is not compromised. Thus this system of incorporating two or more peristaltic pump tubes helps in attaining a higher flow rate for a relatively lesser RPM. It is but obvious that the said two or more than two parallel tubes are connected to each other at the inlet and the outlet ends of the peristaltic pump.

Determination of the Instantaneous Real Time Rate of Fluid Intravasation

Fluid intravasation is a process by which the irrigation fluid enters into the patient's body system and if excess volume of fluid is intravasated it can be dangerous to the patient's life. Thus, keeping in mind surgical safety, it is extremely important to constantly know the rate at which such intravasation occurs so that corrective surgical measures can be taken before a dangerous volume of fluid intravasates. The inventors propose that one fluid flow rate sensor each be incorporated in the inflow tube and the outflow tube. Referring to FIGS. 1 and 2 the inflow flow rate sensor could be located anywhere in the inflow tube 10 between the inlet port of the endoscope and the outlet end of pump 4. Such a flow rate sensor would measure the rate at which fluid enters into the tissue cavity 8 and the same is being termed as 'cavity inflow rate'. Similarly the outflow flow rate sensor could be located anywhere in the out flow tube. The outflow flow rate sensor measures the rate at which fluid exits from the tissue cavity, and let the same be termed as the 'cavity outflow rate'. Now the real time rate of fluid intravasation, being termed as R3, can be determining by subtracting the 'cavity outflow rate' from the 'cavity inflow rate', the mathematical expression for the same being can be written as R3='Cavity inflow rate'–'Cavity outflow rate'. The said flow rate sensors should be accurate, reliable, easy to install and should not have any movable parts. The inventors suggest that a the said sensor comprise of a heating coil in physical contact with a metal plate for heating the same and a temperature sensor placed in contact with the metal plate, the temperature of the metal plate being a function of the fluid flow rate. The said flow rate sensors are electrically connected with a micro-controller which automatically subtracts the 'Cavity outflow rate' from the 'cavity inflow rate' to give the value R3. The value can also be further integrated with respect to time to give the total volume of fluid intravasated over a certain time interval. The said temperature related flow rate sensor could be a 'hot wire anemometer'. The inflow fluid flow rate sensor could also be avoided if the 'Cavity inflow rate' related information was to be derived from the RPM of the inflow pump 4. For any positive displacement pump, like a peristaltic pump, the pump flow rate is directly proportional to the pump RPM. The said inflow fluid flow rate sensors, like hot wire anemometers, have not been included in any of the drawings only to keep the drawings simple.

The proposed invention can also be used to impart endoscopic training skills by the help of endoscopic experimental models based on the present invention. Also use and scope of the present invention is not limited to human tissue cavities and it may be used for performing multiple endoscopic procedures in animal tissue cavities also and also for imparting training in endoscopic surgeries related to animal tissue cavities.

It is believed that the foregoing description conveys the best understanding of the objects and the advantages of the present invention. It will be understood by those skilled in the art that numerous improvements and modifications may be made to the embodiments of the invention disclosed herein without departing from the departing from the spirit and scope thereof.

The Invention is Unique

There is no other prior art system in which the amplitude of pressure pulsations produced by a positive displacement, like a peristaltic pump, could be minimized to a negligible level by using a 'pressure pulse dampening system' as described. Also determination of the instantaneous rate of fluid intravasation by using hot wire anemometers and the concept of installing two or more peristaltic tubes in parallel have not been described in any prior art system.

The Heart and Soul of the Invention

The 'pressure pulse dampening system' using a syringe mechanism is the heart and soul of the invention without which the invention cannot exist.

Advantages of the Proposed Invention

The proposed invention makes endoscopic procedures extremely safe, simple, more accurate and easy to perform. The proposed invention helps the surgeons to perform endoscopic surgeries with greater safety and confidence especially in the initial phase of their learning curve. Also a distending system based on the proposed invention can be used in multiple endoscopic procedures thus reducing the financial burden on the hospital and the patient. The advantages of proposed invention are summarized in the following table along with the corresponding disadvantages of the prior art systems:

| ADVANTAGES OF THE PRESENT INVENTION: | DISADVANTAGES OF THE PRIOR ART SYSTEMS: |
| --- | --- |
| It is possible to reduce the amplitude of the pressure pulsations created by a positive displacement pump to an almost negligible magnitude irrespective of the pump RPM. | This is not possible in any prior art system. |
| It is possible to minimize cavity fluid turbulence to almost negligible levels. | This is not possible in any prior art system. |
| It is possible to reduce the frequency of the pressure pulsations created by an outflow positive displacement pump for the same outflow rate. | This is not possible in any prior art system. |
| /The instantaneous real time rate of fluid intravasation into the patient's body is constantly known by using a hot wire anemometer type of a flow rate sensor. | Such feature is not present in any prior art system. |

CONCLUSION

The proposed invention is novel and unique. The invention relates not only to increasing surgical efficiency in certain endoscopic procedures but it also helps in preventing human morbidity and human mortality in many endoscopic procedures. Thus the proposed invention is extremely useful for entire mankind.

We claim:

1. A system for distending body tissue cavities of subjects by continuous flow irrigation during endoscopic procedures, the system comprising:

a fluid source reservoir containing a non viscous physiologic fluid; a fluid supply tube connecting the fluid source reservoir to an inlet end of a variable speed positive displacement inflow pump and an outlet end of the inflow pump being connectable to an inflow port through an inflow tube for pumping the fluid into the cavity; an outflow port connectable to a waste fluid collecting container via a waste fluid tube; and an active inflow pressure pulsation dampening means having only one opening, said only one opening connected to the inflow tube for dampening the pressure pulsations inside the cavity created by the positive displacement inflow pump only.

2. The system as claimed in claim 1, wherein the fluid source reservoir containing the non-viscous physiologic fluid is maintained at atmospheric pressure or at a pressure greater than the atmospheric pressure.

3. The system as claimed in claim 1, wherein a proximal open end of the fluid supply tube is connected to the fluid source reservoir and a distal end of the tube is connected to the inlet end of the variable speed positive displacement inflow pump.

4. The system as claimed in claim 3, wherein the proximal open end of the fluid supply tube is immersed in the fluid source reservoir.

5. The system as claimed in claim 1, wherein a proximal end of the inflow tube is connected to the outlet end of the variable speed positive displacement inflow pump and a distal end of the inflow tube is connected to the inflow port.

6. The system as claimed in claim 1, wherein the variable speed positive displacement inflow pump is selected from the group consisting of peristaltic pump, piston pump, gear pump and diaphragm pump.

7. The system as claimed in claim 6, wherein the variable speed positive displacement inflow pump is a peristaltic pump.

8. The system as claimed in claim 1, further comprising an inflow pressure transducer located away from the cavity site, near the outlet end of the inflow pump, such that pressure inside the cavity is measured.

9. The system as claimed in claim 1, wherein a proximal end of the waste fluid tube is connected to the outlet end and a distal end of the waste fluid tube is connected to the waste fluid collecting container.

10. The system as claimed in claim 1, further comprising a micro-controller electrically coupled to the inflow pump for regulating the operation of the inflow pump.

11. The system as claimed in claim 1, wherein the fluid supply tube, the inflow tube and the waste fluid tube are flexible, disposable and are made of polymeric material.

12. The system as claimed in claim 1, wherein the active inflow pressure pulsation dampening means comprises a single outlet syringe, the piston of the same being coupled to the positive displacement inflow pump in a synchronous manner through a coupling means in such manner so that movement of the piston is not influenced by the fluid pressure at the outlet end of the inflow pump, and a single outlet end of the syringe being connected to the inflow tube.

13. The system as claimed in claim 1, wherein the active inflow pressure pulsation dampening means is connected to the inflow tube between the outflow end of the peristaltic pump and an inflow pressure transducer.

14. The system as claimed in claim 1, wherein the fluid source reservoir, the inflow pump, the fluid supply tube, the inflow tube and the tissue cavity are placed approximately at the same height with respect to a horizontal ground.

15. The system as claimed in claim 7 wherein the peristaltic pump is provided with one to five peristaltic pump tribes connected in parallel between the inflow and outflow ends of the peristaltic pump for reducing the frequency of pulsations in the pressure, the tubes being connected to each other at the inflow and outflow ends of the peristaltic pump, and the peristaltic pump tubes contacting the rollers of the peristaltic pump.

* * * * *